United States Patent
Liao et al.

(10) Patent No.: US 11,739,037 B1
(45) Date of Patent: Aug. 29, 2023

(54) METHOD FOR MANUFACTURING NONYLCYCLOHEXANOL

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Jung-Tsu Wu, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 17/991,816

(22) Filed: Nov. 21, 2022

(30) Foreign Application Priority Data

Jul. 4, 2022 (TW) .................................. 111124871

(51) Int. Cl.
*C07C 29/20* (2006.01)
*B01J 8/10* (2006.01)
*B01J 23/46* (2006.01)

(52) U.S. Cl.
CPC .................. *C07C 29/20* (2013.01); *B01J 8/10* (2013.01); *B01J 23/464* (2013.01)

(58) Field of Classification Search
CPC .................................. C07C 29/19; C07C 29/20
See application file for complete search history.

(56) References Cited

U.S. PATENT DOCUMENTS

| 5,942,645 | A | * | 8/1999 | Rutter | .................. B01J 23/462 |
| | | | | | 568/822 |
| 2018/0057438 | A1 | | 3/2018 | Liao et al. |

FOREIGN PATENT DOCUMENTS

| CN | 103435449 A | 12/2013 | |
| CN | 104151134 A | * 11/2014 | .............. C07C 29/20 |
| CS | 213247 B1 | * 3/1982 | ................ B01J 8/10 |
| TW | 201808873 A | 3/2018 | |

OTHER PUBLICATIONS

CN104151134A, machine translation, Nov. 2014, pp. 1-7 (Year: 2014).*
CN103435449A, machine translation, Dec. 2013, pp. 1-4 (Year: 2013).*
CS213247B1, machine translation, Mar. 1982, pp. 1-2 (Year: 1982).*

* cited by examiner

*Primary Examiner* — Medhanit W Bahta
(74) *Attorney, Agent, or Firm* — Li & Cai Intellectual Property Office

(57) ABSTRACT

A method for manufacturing nonylcyclohexanol is provided. The method includes steps as follows: adding a liquid phase reactant into a reactor, and the liquid phase reactant includes a molten nonylphenol and a catalyst; introducing a gas phase reactant to maintain a pressure of the gas phase reactant to be from 36.5 bar to 70 bar, and the gas phase reactant consists of hydrogen; rotating a hollow stirring shaft of the reactor at a temperature of from 100° C. to 130° C. so that the gas phase reactant is transported through a channel formed in the hollow stirring shaft into the liquid phase reactant for carrying out a reaction; obtaining a product that contains nonylcyclohexanol. A conversion rate of the nonylcyclohexanol is higher than or equal to 99.0%.

10 Claims, 2 Drawing Sheets

METHOD FOR MANUFACTURING NONYLCYCLOHEXANOL

CROSS-REFERENCE TO RELATED PATENT APPLICATION

This application claims the benefit of priority to Taiwan Patent Application No. 111124871, filed on Jul. 4, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for manufacturing nonylcyclohexanol, and more particularly to a method for manufacturing nonylcyclohexanol having a high conversion rate.

BACKGROUND OF THE DISCLOSURE

Nonylphenol is a main material for manufacturing nonylphenol polyethoxylates (NPEO). Nonylphenol polyethoxylates are mainly used as nonionic surfactants in industrial detergents. In addition, nonylphenol polyethoxylates can also be applied to antioxidants, auxiliaries for printing and dyeing textiles, additives for lubricating oil, pesticide emulsifiers, resin modifiers, resin and rubber stabilizers, etc.

Although nonylphenol has low toxicity, it is defined as one of endocrine disruptors due to having a chemical structure similar to that of estrogen. Due to the long-time usage of nonylphenol in the past, the natural environment has been polluted by nonylphenol-containing wastewater, and the presence of nonylphenol is discovered in rivers, farmlands, and crops. Based on the idea of environmental protection, developing a detergent raw material without endocrine disruptors is one of the goals in relevant fields of research.

In order to address the issue of environmental pollution, nonylcyclohexanol having a structure similar to that of nonylphenol has gradually received more attention. Nonylcyclohexanol has similar interfacial properties to nonylphenol, but has lower biotoxicity and higher biodegradability than nonylphenol. Therefore, nonylcyclohexanol has gradually replaced nonylphenol in use.

A conventional fixed-bed reactor is commonly used for manufacturing nonylcyclohexanol. In a high-temperature environment, a nonylphenol reaction solution (including nonylphenol and a solvent) is reacted with hydrogen under the effect of a catalyst to generate nonylcyclohexanol.

However, in the conventional fixed-bed reactor, the nonylphenol reaction solution has low contact efficiency with hydrogen, resulting in a long reaction time and a limited conversion rate. In practical applications, a poor heat transfer effect often causes non-uniform temperature distribution in the conventional fixed-bed reactor, such that a reaction is difficult to be controlled. Moreover, a disadvantage of a catalyst fixed bed is that it cannot be replaced easily.

Therefore, how to improve the steps to address a low contact efficiency between a nonylphenol reaction solution and hydrogen, has become one of the issues to be addressed in the business.

SUMMARY OF THE DISCLOSURE

In response to the above-referenced technical inadequacies, the present disclosure provides a method for manufacturing nonylcyclohexanol.

In one aspect, the present disclosure provides a method for manufacturing nonylcyclohexanol. The method includes steps as follows: adding a liquid phase reactant into a reactor, and the liquid phase reactant includes a molten nonylphenol and a catalyst; introducing a gas phase reactant to maintain a pressure of the gas phase reactant to be from 36.5 bar to 70 bar, the gas phase reactant consists of hydrogen; rotating a hollow stirring shaft of the reactor at a temperature of from 100° C. to 130° C. so that the gas phase reactant is transported through a channel formed in the hollow stirring shaft into the liquid phase reactant for carrying out a reaction; and obtaining a product that contains nonylcyclohexanol. A conversion rate of the nonylcyclohexanol is higher than or equal to 99.0%.

In certain embodiments, the method further includes: heating nonylphenol at a temperature of from 50° C. to 70° C. to obtain the molten nonylphenol. The liquid phase reactant does not include a solvent.

In certain embodiments, the catalyst is suspended and dispersed in the molten nonylphenol, and the method further includes filtering and separating the catalyst to obtain the product.

In certain embodiments, a content of the catalyst in the liquid phase reactant ranges from 0.1 wt% to 0.5 wt%.

In certain embodiments, the hollow stirring shaft is rotated at a rotational speed of from 800 rpm to 1,200 rpm.

In certain embodiments, the channel includes an axial channel and a plurality of radial channels, the axial channel is in fluid communication with the plurality of radial channels, and the gas phase reactant is transported through the axial channel and the plurality of radial channels into the liquid phase reactant for carrying out the reaction.

In certain embodiments, the hollow stirring shaft provided has a plurality of suction holes formed thereon, and the gas phase reactant enters the axial channel formed in the hollow stirring shaft through the plurality of suction holes.

In certain embodiments, the hollow stirring shaft has a plurality of exhaust holes formed thereon, and the gas phase reactant enters the radial channels formed in the hollow stirring shaft through the plurality of exhaust holes.

In certain embodiments, the hollow stirring shaft is formed by a body that includes a shaft part and a plurality of fan blade parts, one end of the shaft part is connected to a top end of the reactor, and the plurality of fan blade parts are connected to another end of the shaft part. A height of liquid surface of the liquid phase reactant is greater than a height of the plurality of fan blade parts in the reactor.

In certain embodiments, the catalyst is a hydrogenation catalyst containing a metal of palladium or rhodium.

One of the beneficial effects of the present disclosure is that, in the method for manufacturing nonylcyclohexanol, by virtue of "the liquid phase reactant including a molten nonylphenol and a catalyst," and "rotating a hollow stirring shaft of the reactor at a temperature of from 100° C. to 130° C. so that the gas phase reactant is transported through a channel formed in the hollow stirring shaft into the liquid phase reactant for carrying out a reaction," the conversion rate of nonylcyclohexanol can be increased.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
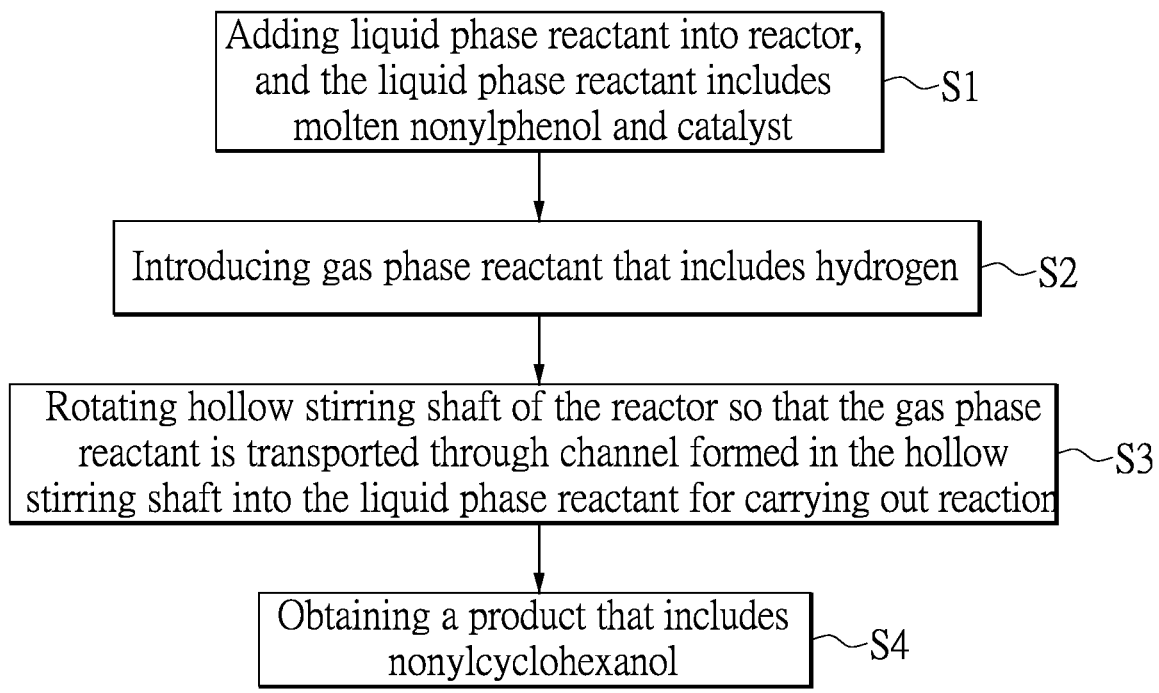
FIG. 1 is a flowchart of a method for manufacturing nonylcyclohexanol according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

In the method for manufacturing nonylcyclohexanol provided by the present disclosure, by using a hollow stirring shaft, a contact efficiency of a liquid phase reactant with a gas phase reactant is increased, and a high conversion rate is achieved in a relatively short reaction time. Moreover, the present disclosure addresses the existing problems of a fixed-bed reactor in use having poor heat transfer effect and causing a non-uniform temperature distribution, and that the catalyst fixed bed cannot be replaced easily.

Referring to FIG. 1, the method for manufacturing nonylcyclohexanol of the present disclosure includes steps as follows: adding a liquid phase reactant into a reactor, and the liquid phase reactant includes a molten nonylphenol and a catalyst (Step S1); introducing a gas phase reactant, the gas phase reactant includes hydrogen (Step S2); rotating a hollow stirring shaft of the reactor so that the gas phase reactant is transported through a channel formed in the hollow stirring shaft into the liquid phase reactant for carrying out a reaction (Step S3); and obtaining a product that contains nonylcyclohexanol (Step S4).

In Step S1, a molten nonylphenol is used as a reactant, and compared to an existing nonylphenol reaction solution in which nonylphenol is dissolved in a solvent, the use of a solvent is excluded in the present disclosure. As such, the concentration of nonylphenol in the liquid phase reactant can be significantly increased to accelerate the reaction. In addition, by using the molten nonylphenol as a reactant, the use and energy consumption of purification devices for distillation and the like can be saved. In some embodiments, a cyclic filtering device may be optionally added.

Moreover, compared with a nonylphenol reaction solution in which nonylphenol is dissolved in a solvent, the molten nonylphenol in the present disclosure promotes the catalyst to be uniformly dispersed in suspension in the molten nonylphenol. When the catalyst is uniformly dispersed in the molten nonylphenol, a good catalytic effect can be achieved.

Similarly, for the purpose of uniform dispersion of the catalyst, a content of the catalyst in the liquid phase reactant is controlled to be from 0.1 wt% to 0.5 w%; and when the content of the catalyst is within this range, a good balance can be achieved between the catalytic effect and the dispersion effect. However, the present disclosure is not limited thereto.

In the method for manufacturing nonylcyclohexanol of the present disclosure, the nonylcyclohexanol is manufactured through hydrogenation. Therefore, the catalyst may be a hydrogenation catalyst that contains a metal of palladium or rhodium. However, the present disclosure is not limited thereto.

In order to obtain the liquid phase reactant in Step S1, a molten nonylphenol can be obtained by heating. For example, a solid nonylphenol is added into the reactor, and then the nonylphenol is heated at a temperature of from 50° C. to 70° C. to obtain the molten nonylphenol.

In Step S2, the gas phase reactant includes hydrogen. In a preferred embodiment, the gas phase reactant consists of hydrogen, and when the gas phase reactant only includes hydrogen, the reaction can be accelerated.

Since the reactor accommodates the liquid phase reactant and the gas phase reactant, maintaining stability between the liquid phase reactant and the gas phase reactant becomes very crucial.

In one exemplary embodiment, after a gas phase reactant is introduced, a pressure of the gas phase reactant is maintained to be from 36.5 bar to 70 bar. For example, the pressure of the gas phase reactant may be 50 bar, 52 bar, 54 bar, 56 bar, 58 bar, 60 bar, 62 bar, 64 bar, 66 bar, or 68 bar. By adjusting the pressure of the gas phase reactant, the conversion rate of nonylcyclohexanol can be further increased.

In Step S3, the temperature of the reactor is increased to be from 100° C. to 130° C., and the hollow stirring shaft of the reactor is rotated so that the liquid phase reactant and the gas phase reactant are mixed with each other for a reaction, to prepare nonylcyclohexanol. In one exemplary embodiment, a rotational speed of the hollow stirring shaft can be set to be from 800 rpm to 1,200 rpm.

Figure 2:
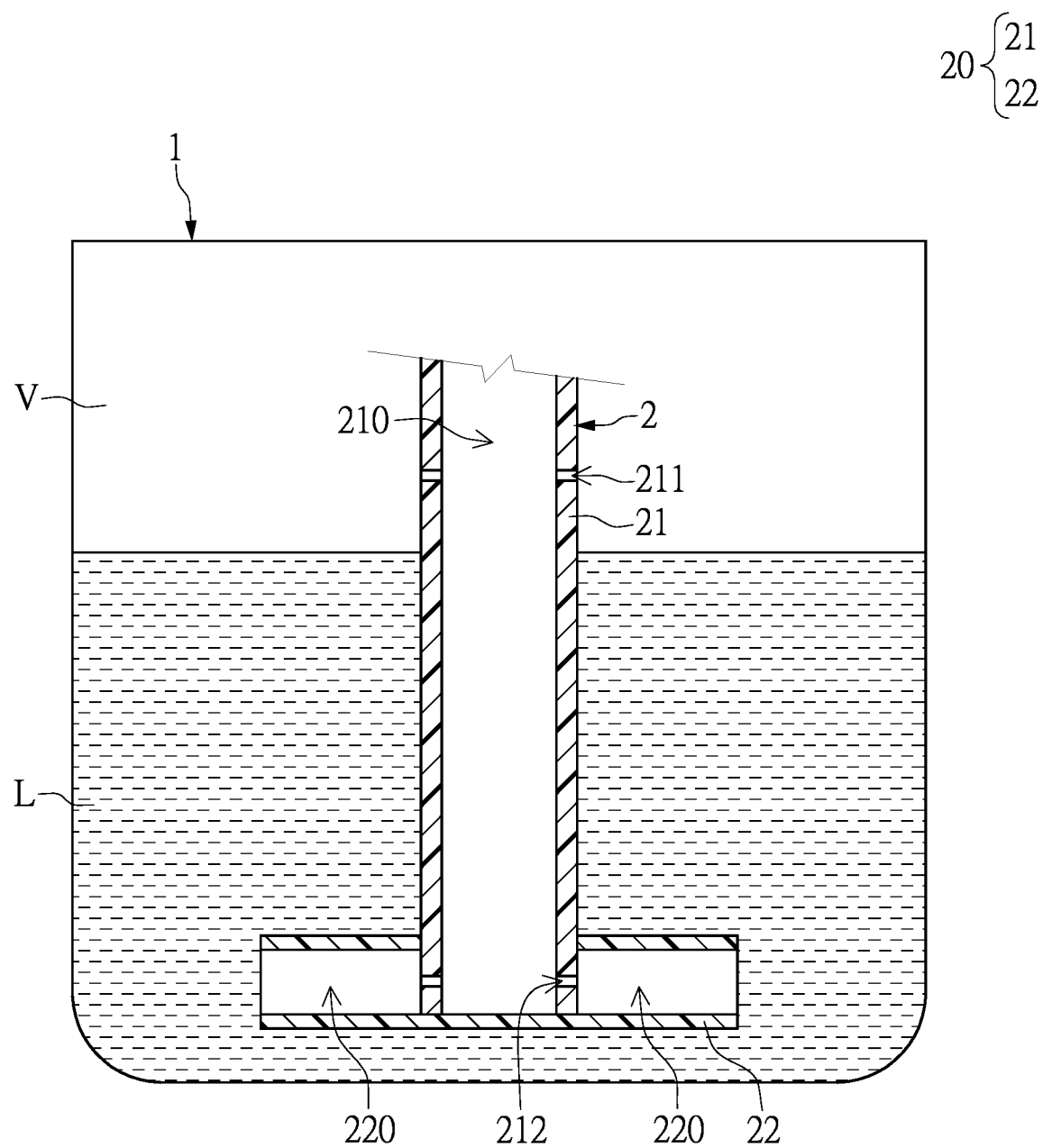
FIG. 2 is a cross-sectional view of a reactor used in the method for manufacturing nonylcyclohexanol according to the present disclosure.

Referring to FIG. 2, a reaction space is formed in a reactor 1 to accommodate a liquid phase reactant L and a gas phase reactant V. A hollow stirring shaft 2 is disposed in the reactor 1, and the hollow stirring shaft 2 can be rotated in the reaction space for an effect of stirring.

The hollow stirring shaft 2 is formed by a body 20, and the body 20 includes a shaft part 21 and a plurality of fan blade parts 22. One end of the shaft part 21 is connected to a top end of the reactor 1 and electrically connected to a controller for adjusting the rotational speed of the hollow stirring shaft 2. The plurality of fan blade parts 22 are connected to the other end of the shaft part 21, and when the hollow stirring shaft 2 rotates, the plurality of fan blade parts 22 can achieve an effect of stirring. In addition, in order to achieve a good stirring effect, a height of a liquid surface of the liquid phase reactant L is greater than a height of the plurality of fan blade parts in the reactor 22.

Specifically, a channel is formed in the hollow stirring shaft 2, and the channel includes an axial channel 210 and a plurality of radial channels 220. The axial channel 210 is formed in the shaft part 21, the radial channels 220 are formed in the fan blade parts 22, and the axial channel 210 is in fluid communication with the plurality of radial channels 220.

Accordingly, during rotation of the hollow stirring shaft 2, under the effect of an air flow around the hollow stirring shaft 2, the gas phase reactant V can enter the axial channel 210 through a plurality of suction holes 211 in the shaft part 21. Next, the gas phase reactant V can respectively enter the corresponding plurality of radial channels 220 through a plurality of exhaust holes 212 in the shaft part 21. Finally, the gas phase reactant V can be transported into the liquid phase reactant L, so that the gas phase reactant V and the liquid phase reactant L are mixed with each other for carrying out a reaction.

That is to say, in the step (Step S3) of rotating the hollow stirring shaft 2, the gas phase reactant V not only can react around a periphery of a liquid-gas interface formed by the gas phase reactant V and the liquid phase reactant L, but also can react with the liquid phase reactant L around a periphery of the fan blade parts 22 through the channel in the hollow stirring shaft 2. Therefore, the method for manufacturing nonylcyclohexanol of the present disclosure can effectively increase a contact efficiency between the liquid phase reactant and the gas phase reactant, thereby achieving a high conversion rate within a short reaction time.

In Step S4, after the reaction in Step S3, a product containing nonylcyclohexanol can be obtained. Since the catalyst is still suspended and dispersed in nonylcyclohexanol, the catalyst can be recovered through filtration and separation processes for obtaining a product having a high content of nonylcyclohexanol. In the present disclosure, a conversion rate of the nonylcyclohexanol is higher than or equal to 99.0%.

Examples 1 to 3 below are made according to the above-mentioned steps S1 to S4 in order to prove that the present disclosure can be used for manufacturing nonylcyclohexanol having a high conversion rate, and specific steps are described as follows.

[Example 1]

360 g of nonylphenol and 10.8 g of a rhodium catalyst were added into a reactor with a volume of 0.5 L, hydrogen was introduced into the reactor, and a pressure of the hydrogen in the reactor was maintained at 590 psi. Next, a temperature of the reactor was increased to 50° C. and maintained for 15 minutes, so as to form a molten nonylphenol.

A hollow gas stirrer in the reactor was started, and a rotational speed of the hollow gas stirrer was set to 1,000 rpm. The temperature of the reactor was further increased to 120° C., and a reaction was allowed to be carried out for 5 hours under continuous rotation of the hollow gas stirrer.

After the reaction was carried out, when the temperature of the product was cooled to room temperature, the catalyst was separated by filtration, and then the composition of the product was analyzed. As shown in the analysis results, a conversion rate of nonylcyclohexanol in Example 1 is 99.5%.

[Example 2]

360 g of nonylphenol and 10.8 g of a rhodium catalyst were added into a reactor with a volume of 0.5 L, hydrogen was introduced into the reactor, and a pressure of the hydrogen in the reactor was maintained at 530 psi. Next, a temperature of the reactor was increased to 50° C. and maintained for 15 minutes, so as to form a molten nonylphenol.

A hollow gas stirrer in the reactor was started, and a rotational speed of the hollow gas stirrer was set to 1,000 rpm. The temperature of the reactor was further increased to 120° C., and a reaction was allowed to be carried out for 5 hours under continuous rotation of the hollow gas stirrer.

After the reaction was carried out, when the temperature of the product was cooled to room temperature, the catalyst was separated by filtration, and then the composition of the product was analyzed. As shown in the analysis results a conversion rate of nonylcyclohexanol in Example 2 is 99.0%.

[Example 3]

360 g of nonylphenol and 10.8 g of a rhodium catalyst were added into a reactor with a volume of 0.5 L, hydrogen was introduced into the reactor, and a pressure of the hydrogen in the reactor was maintained at 650 psi. Next, a temperature of the reactor was increased to 50° C. and maintained for 15 minutes, so as to form a molten nonylphenol.

A hollow gas stirrer in the reactor was started, and a rotational speed of the hollow gas stirrer was set to 1,000 rpm. The temperature of the reactor was further increased to 120° C., and a reaction was allowed to be carried out for 5 hours under continuous rotation of the hollow gas stirrer.

After the reaction was carried out, when the temperature of the product was cooled to room temperature, the catalyst was separated by filtration, and then the composition of the product was analyzed. As shown in the analysis results, a conversion rate of nonylcyclohexanol in Example 3 is 99.9%.

As shown in the results of Examples 1 to 3, the use of the hollow stirring shaft in the present disclosure can increase the contact efficiency of the liquid phase reactant with the gas phase reactant, and thus increase the conversion rate of nonylcyclohexanol to be higher than or equal to 99.0%. Moreover, by adjusting the pressure of hydrogen in the reactor to be from 50 bar to 68 bar, the conversion rate of nonylcyclohexanol can be further increased. Preferably, the pressure of hydrogen in the reactor is maintained at from 58 bar to 67 bar.

[Beneficial Effects of the Embodiments]

One of the beneficial effects of the present disclosure is that, in the method for manufacturing nonylcyclohexanol, by virtue of "the liquid phase reactant including a molten nonylphenol and a catalyst," and "rotating a hollow stirring shaft of the reactor at a temperature of from 100° C. to 130° C. so that the gas phase reactant is transported through a channel formed in the hollow stirring shaft into the liquid phase reactant for carrying out a reaction" the conversion rate of nonylcyclohexanol can be increased.

Further, the present disclosure excludes the use of a solvent, and adopts a molten nonylphenol for a reaction, such that the concentration of nonylphenol in the liquid phase reactant can be significantly increased, and the reaction can be accelerated. Moreover, the molten nonylphenol facilitates the catalyst to be uniformly dispersed in suspension in the molten nonylphenol.

Further, the present disclosure selects a catalyst of specific content and specifications (i.e., having specific surface area and particle size) so that the catalyst can be uniformly dispersed in the liquid phase reactant in suspension and the liquid phase reactant and the gas phase reactant can react with the aid of the catalyst, thereby reducing the reaction time.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for manufacturing nonylcyclohexanol, comprising:
    adding a liquid phase reactant into a reactor, wherein the liquid phase reactant includes a molten nonylphenol and a catalyst;
    introducing a gas phase reactant to maintain a pressure of the gas phase reactant to be from 36.5 bar to 70 bar, wherein the gas phase reactant consists of hydrogen;
    rotating a hollow stirring shaft of the reactor at a temperature of from 100° C. to 130° C. so that the gas phase reactant is transported through a channel formed in the hollow stirring shaft into the liquid phase reactant for carrying out a reaction; and
    obtaining a product that contains nonylcyclohexanol;
    wherein a conversion rate of the nonylcyclohexanol is higher than or equal to 99.0%.

2. The method according to claim 1, further comprising: heating nonylphenol at a temperature of from 50° C. to 70° C. to obtain the molten nonylphenol, wherein the liquid phase reactant does not include a solvent.

3. The method according to claim 1, wherein the catalyst is suspended and dispersed in the molten nonylphenol, and the method further comprises filtering and separating the catalyst to obtain the product.

4. The method according to claim 1, wherein a content of the catalyst in the liquid phase reactant ranges from 0.1 wt% to 0.5 wt%.

5. The method according to claim 1, wherein the hollow stirring shaft is rotated at a rotational speed of from 800 rpm to 1,200 rpm.

6. The method according to claim 1, wherein the channel includes an axial channel and a plurality of radial channels, the axial channel is in fluid communication with the plurality of radial channels, and the gas phase reactant is transported through the axial channel and the plurality of radial channels into the liquid phase reactant for carrying out the reaction.

7. The method according to claim 6, wherein the hollow stirring shaft has a plurality of suction holes formed thereon, and the gas phase reactant enters the axial channel formed in the hollow stirring shaft through the plurality of suction holes.

8. The method according to claim 6, wherein the hollow stirring shaft has a plurality of exhaust holes formed thereon, and the gas phase reactant enters the radial channels formed in the hollow stirring shaft through the plurality of exhaust holes.

9. The method according to claim 1, wherein the hollow stirring shaft is formed by a body that includes a shaft part and a plurality of fan blade parts, one end of the shaft part is connected to a top end of the reactor, and the plurality of fan blade parts are connected to another end of the shaft part; wherein a height of a liquid surface of the liquid phase reactant is greater than a height of the plurality of fan blade parts in the reactor.

10. The method according to claim 1, wherein the catalyst is a hydrogenation catalyst containing a metal of palladium or rhodium.

\* \* \* \* \*